(12) United States Patent
Van Den Heuvel

(10) Patent No.: US 12,375,196 B2
(45) Date of Patent: Jul. 29, 2025

(54) BROADCAST SELECTION

(71) Applicant: Cochlear Limited, Macquarie University (AU)

(72) Inventor: Koen Erik Van Den Heuvel, Hove (BE)

(73) Assignee: Cochlear Limited, Macquarie University (AU)

( * ) Notice: Subject to any disclaimer, the term of this patent is extended or adjusted under 35 U.S.C. 154(b) by 253 days.

(21) Appl. No.: 18/041,323

(22) PCT Filed: Aug. 18, 2021

(86) PCT No.: PCT/IB2021/057590
§ 371 (c)(1),
(2) Date: Feb. 10, 2023

(87) PCT Pub. No.: WO2022/038533
PCT Pub. Date: Feb. 24, 2022

(65) Prior Publication Data
US 2023/0269013 A1  Aug. 24, 2023

Related U.S. Application Data

(60) Provisional application No. 63/067,007, filed on Aug. 18, 2020.

(51) Int. Cl.
*H04H 40/27* (2008.01)
*A61N 1/05* (2006.01)
(Continued)

(52) U.S. Cl.
CPC ............ *H04H 40/27* (2013.01); *H04H 20/71* (2013.01); *A61N 1/0541* (2013.01); *A61N 1/0543* (2013.01);
(Continued)

(58) Field of Classification Search
CPC ...... H04H 40/27; H04H 20/71; A61N 1/0541; A61N 1/0543; H04R 25/554; H04R 2225/67
(Continued)

(56) References Cited

U.S. PATENT DOCUMENTS 4,955,070 A * 9/1990 Welsh .................... H04H 60/44
455/2.01
10,003,894 B2 6/2018 Case et al.
(Continued)

FOREIGN PATENT DOCUMENTS

EP 2499841 B1 9/2015
EP 3629602 A1 4/2020

OTHER PUBLICATIONS

International Search Report and Written Opinion in counterpart International Application No. PCT/IB2021/057590, mailed Nov. 23, 2021, 9 pages.

*Primary Examiner* — Kam Wan Ma
(74) *Attorney, Agent, or Firm* — Edell, Shapiro & Finnan, LLC

(57) ABSTRACT

Disclosed technology includes a sensory prosthesis configured to automatically select a broadcast channel based on a comparison with a signal from a sensor of the sensory prosthesis. In an example, a sound processor automatically connects to an appropriate wireless broadcast audio channel by comparing the sound the sound processor receives on a microphone with the audio the sound processor receives from each of the wireless broadcast channels that the sound processor can receive. If the sound processor finds a match between the sound from the microphone and the sound from a broadcast, then the sound processor automatically selects the matching wireless broadcast channel. The sound proces-
(Continued)

sor then provides auditory stimulation to the recipient based on the selected broadcast channel.

30 Claims, 8 Drawing Sheets

(51) Int. Cl.
 *H04H 20/71* (2008.01)
 *H04R 25/00* (2006.01)
(52) U.S. Cl.
 CPC ........ *H04R 25/554* (2013.01); *H04R 2225/67* (2013.01)
(58) Field of Classification Search
 USPC .......................................... 340/4.1
 See application file for complete search history.

(56) References Cited

U.S. PATENT DOCUMENTS

| | | |
|---|---|---|
| 10,713,936 B2 | 7/2020 | Banna et al. |
| 2005/0207602 A1 | 9/2005 | van Oerle |
| 2011/0004271 A1 | 1/2011 | Dapper et al. |
| 2014/0325354 A1* | 10/2014 | Zhang .................... G06F 3/038 715/716 |
| 2014/0341405 A1* | 11/2014 | Pedersen ................ H04H 60/44 381/315 |
| 2015/0195641 A1* | 7/2015 | Di Censo ............. H04R 1/1083 381/71.6 |
| 2017/0171674 A1* | 6/2017 | Fung .................... H04R 25/507 |

* cited by examiner

BROADCAST SELECTION

BACKGROUND

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In an example, there is a method comprising: determining that a broadcast sample and a sensor sample match; and selecting a broadcast associated with the broadcast sample responsive to the broadcast sample and the sensor sample match.

In another example, there is a computer-readable medium having instructions stored thereon that, when executed by one or more processors, cause the one or more processors to: check for a set of candidate broadcasts; and for each respective broadcast of the set of candidate broadcasts: obtain a broadcast sample from the respective broadcast; obtain a sensor sample from a sensor; compare the broadcast sample and the sensor sample; and select the respective broadcast responsive to the comparing indicating that the broadcast sample and the sensor sample match.

In a further example, there is a system comprising: a sensory prosthesis; a sensor; a receiver; and one or more processors. The one or more processors are configured to: obtain a broadcast sample from the receiver; obtain a sensor sample from the sensor; determine whether the broadcast sample and the sensor sample match; and select, as a source used by the sensory prosthesis to cause a person to experience a sensory percept, a broadcast associated with the broadcast sample responsive to the broadcast sample and the sensor sample matching.

BRIEF DESCRIPTION OF THE DRAWINGS

The same number represents the same element or same type of element in all drawings.

DETAILED DESCRIPTION

Figure 1:
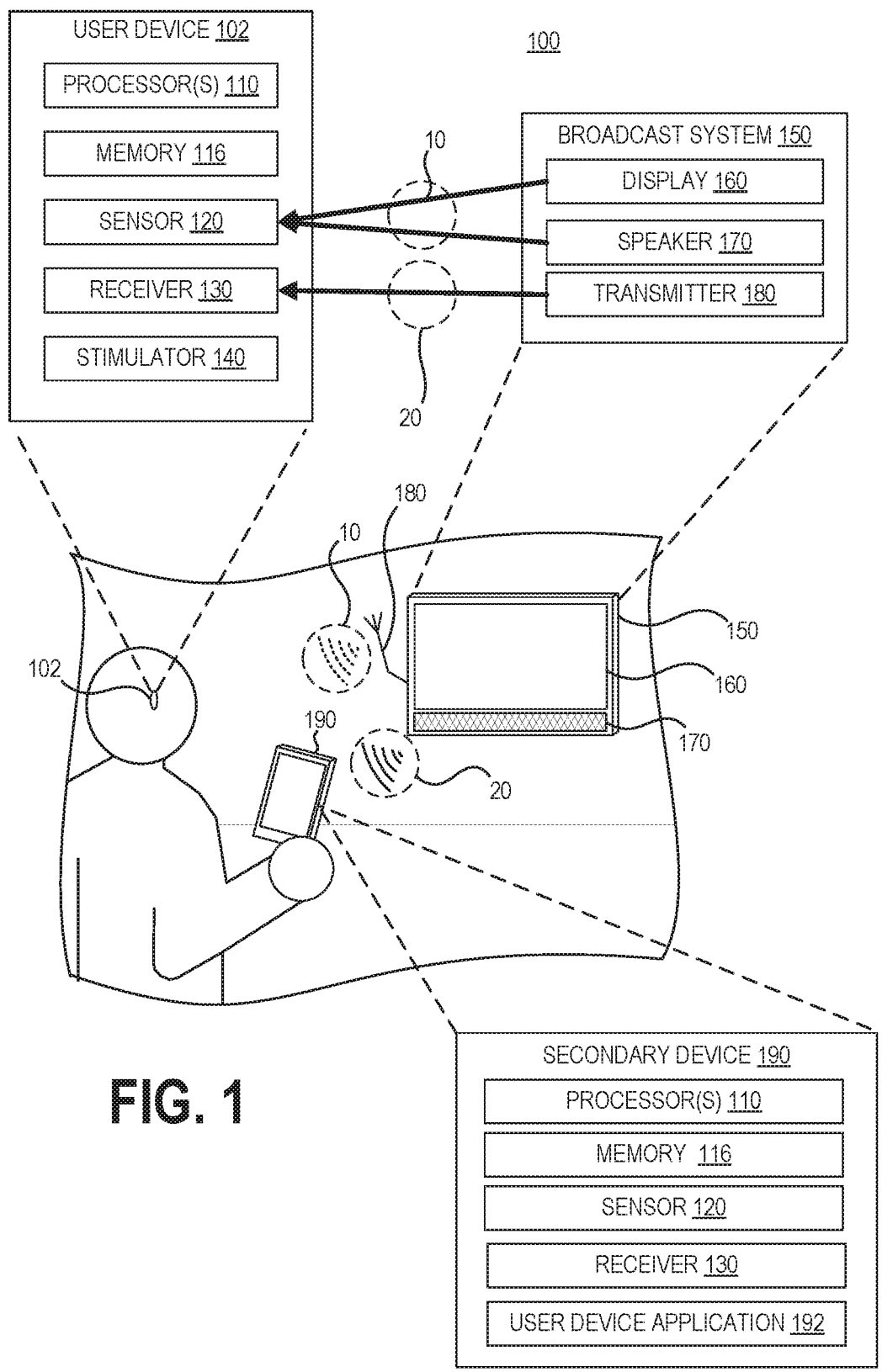
FIG. 1 illustrates an example system that includes a user device, a broadcast system, and a secondary device.

Disclosed technology includes a user device configured to automatically select a broadcast channel based on a comparison with a signal from one or more sensors of the user device, such as a consumer device or a sensory prosthesis. Example consumer devices include headphones, earbuds, personal sound amplification products, wireless earbuds, or other consumer devices. Example sensory prostheses include auditory prostheses and visual prostheses.

A sensory prosthesis provides sensory stimulation to its recipient. Such stimulation is typically provided based on data obtained from one or more sensors of the sensory prosthesis. An auditory prosthesis, such as a hearing aid or cochlear implant, receives audio data from one or more microphones and uses the audio data to deliver stimulation, for instance. But some sensory prostheses can be configured to provide stimulation based on data received from one or more wireless transmissions. For instance, a recipient of a visual prosthesis wirelessly streams video from the recipient's phone, such that the stimulation from the visual prosthesis is based on the wireless stream from the phone in addition to or instead of data from a camera of the visual prosthesis. In many examples, data received wirelessly from another device is of higher quality than data produced by the prosthesis's sensors (e.g., because the wireless data remains digital rather than being converted to an analog signal, transmitted in an analog manner, received as an analog signal, and then is converted to a digital signal). For instance, a theater may provide audio via standard theater speakers as well as audio via a wireless broadcast using BLUETOOTH. A recipient of a cochlear implant watching a movie at that theater may prefer to receive auditory stimulation based on the wireless broadcast compared to audio received through one or more microphones of the recipient's sensory prosthesis. In such an instance, the recipient would typically need to be aware of the broadcast and then manually select to receive the transmission via the broadcast.

A non-limiting example of a device being configured to operate based on output from a sensor or output from an accessory device is described in U.S. Pat. No. 8,706,245, which is hereby incorporated herein by reference in its entirety for any and all purposes. The patent describes that, in a first mode of operation, a hearing prosthesis receives a microphone input and produces an output based on the microphone input. In a second mode of operation, the hearing prosthesis detects an accessory input signal and switches to an accessory input mode. The second mode of operation produces an output that is based at least in part on the accessory input signal (e.g., as transmitted over BLUETOOTH). When the accessory input signal is not detected, the hearing prosthesis operates in microphone operation mode.

In an example of technology disclosed herein, a sound processor of an auditory prosthesis automatically connects to an appropriate wireless broadcast audio channel (e.g., a BLUETOOTH audio channel) by comparing the sound the sound processor receives from a microphone of the sound processor with audio that the sound processor receives from each of the wireless broadcast channels that the sound processor can receive. If the sound processor finds a match between the sound from the microphone and the sound from a broadcast, then the sound processor automatically selects the matching wireless broadcast channel. The sound processor then provides auditory stimulation to the recipient based on broadcast audio from the selected broadcast channel in addition to or instead of sensor audio from one or more microphones.

An example system usable with disclosed is shown in FIG. 1.

Example System

FIG. 1 illustrates an example system 100 that includes a user device 102, a broadcast system 150, and a secondary device 190.

The user device 102 is a device of a user that provides stimulation to a user of the user device 102 to cause a sensory percept. For instance, the sensory precepts are related to one or more of the five traditional senses (vision, hearing, touch, taste, and smell) and/or one or more additional senses (e.g., proprioception). For ease of understanding, many examples herein are discussed in the context of auditory percepts and visual percepts. The user device 102 can take any of a variety of forms, such as a consumer device or a medical prosthesis. Example consumer devices include headphones, earbuds, personal sound amplification products, wireless earbuds, or other consumer devices. Example prostheses include auditory prostheses and visual prostheses. Example auditory prostheses include one or more prostheses selected from the group consisting of: a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, and a tooth-anchored hearing device. Example visual prostheses include bionic eyes.

Then user device 102 can include any of a variety of components based on its form and function. In the illustrated example, the user device 102 includes one or more processors 110, memory 116, a sensor 120, a receiver 130, and a stimulator 140.

The one or more processors 110 are one or more hardware or software processing units (e.g., Central Processing Units) that can obtain and execute instructions, such as to communicate with and control the performance of other components of the user device 102 or the system 100. In addition or instead, the one or more processors 110 can include microcontrollers configured to perform one or more operations.

The memory 116 is one or more software- or hardware-based computer-readable storage media operable to store information accessible by the one or more processors 110. The memory 116 can store, among other things, instructions executable by the one or more processors 110 to implement applications or cause performance of operations described herein, as well as other data. The memory 116 can be volatile memory (e.g., RAM), non-volatile memory (e.g., ROM), or combinations thereof. The memory 116 can include transitory memory or non-transitory memory. The memory 116 can also include one or more removable or non-removable storage devices. In examples, the memory 116 includes RAM, ROM, EEPROM (Electronically-Erasable Programmable Read-Only Memory), flash memory, optical disc storage, magnetic storage, solid state storage, or any other memory media usable to store information for later access. In examples, the memory 116 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 116 includes wired media such as a wired network or direct-wired connection, and wireless media such as acoustic, RF, infrared and other wireless media or combinations thereof.

The sensor 120 is a component that generates signals based on sensed occurrences, such as data regarding the environment around the user device 102. In some examples, the sensors 120 are configured to obtain data for the generation of stimulation via the stimulator 140. In addition or instead, the sensor 120 can provide other functionality to the user device 102, such as providing sensing for a communication (e.g., a call or noise cancelation). In an example, the sensor 120 is a microphone. In another example, the sensor 120 is a camera.

The receiver 130 is a component configured to usably receive a wirelessly transmitted signal. Typically, the wirelessly transmitted signal is transmitted in a from not readily perceptible by a person (e.g., because the transmitted signal is outside of the range of typical human senses). In some examples, the receiver 130 is or includes a transmitter or transceiver. In some examples, the receiver 130 includes an antenna, such as an antenna configured to receive radio waves of between 76.0 MHz and 108.0 MHz, between 2.40 GHz and 2.50 GHz, or between 5.00 GHz and 6.00 GHz. In examples, the receiver 130 is configured to receive WI-FI signals, BLUETOOTH signals, or FM signals. In examples, the receiver 130 includes multiple components (e.g., an antenna and a processor). In an example, the receiver 130 is in a system-on-a-chip configuration.

The stimulator 140 is a component configured to cause the recipient of the user device 102 to experience a sensory percept, such as a visual percept or a hearing percept.

In an example, the stimulator 140 is a component configured to provide stimulation to a recipient's auditory system to cause a hearing percept to be experienced by the recipient. Examples of components usable for auditory stimulation include components for generating air-conducted vibrations (e.g., a speaker), components for generating bone-conducted vibration (e.g., an actuator coupled to a conducting pad or anchor), components for generating electrical stimulation (e.g., one or more electrodes), other components, or combinations thereof.

In an example, the stimulator 140 is a component configured to provide visual stimulation to a recipient's visual system to cause a visual percept to be experienced by the recipient. Examples of components usable for visual stimulation include components for generating visible light (e.g., a display), components for generating electrical stimulation (e.g., one or more electrodes), other components, or combinations thereof.

Although the user device 102 is shown as a single structure having multiple components, the user device 102 can take other forms. In some examples, the user device 102 is split into an implantable component (e.g., a cochlear implant implanted in the recipient) and an external component. In further examples, the user device 102 is split into separate left and right components to fit in the recipient's ears (e.g., in the form of earbuds). The user device 102 can further include companion devices, such as a charging case or battery pack. Example implementations of the user device are shown and described in relation to FIGS. 6-8.

The broadcast system 150 is a device or system of devices that provides content via a broadcast signal 10 and a signal 20 of another modality (e.g., via air conducted sound or via visual signal). As illustrated, the broadcast system 150 includes a display 160, a speaker 170, and a transmitter 180. The broadcast system 150 can take other forms and configurations.

In the illustrated example, the broadcast system 150 is a television that provides a visual signal 20 via the display 160, an air-conducted audio signal 20 via the speaker 170, and broadcasts an audio signal similar to the audio signal 20 via a broadcast signal 10. For instance, the broadcast signal 10 uses BLUETOOTH, WI-FI, FM, or another technology to encode and broadcast the sound that also makes up the audio signal 20 via the transmitter 180. In addition or instead, the broadcast signal 10 encodes some or all of the visual signal 20 provided by the display 160. Broadcast device 150 technology is applicable to a variety of circumstances, such as at a home, gym, restaurant, theater, or other location. Similar approaches are applicable to use in classrooms or lecture halls where a person acts as the broadcaster with their natural speaking voice (amplified or unamplified) corresponds to the audio signal 20 and a broadcast system (e.g., via an induction loop, FM transmitter, or BLUETOOTH transmission via isochronous channels) transmits the broadcast signal 10 to people who want to receive the broadcast signal (e.g., individuals having hearing aids). Further examples include transportation facilities (e.g., airports, train stations, or bus terminals) or buildings (e.g., campuses or malls) having a public address system that provides audio signals 20 via speakers and may also provide inaudible broadcast signals 10. The broadcast system 150 can take any of a variety of forms to fit such circumstances. In a further example, the broadcast system 150 is a broadcast system for an airport that includes multiple speakers 170 in various areas of the airport (e.g., for making announcements) and has multiple displays 160 in various areas of the airport (e.g., for displaying the announcements). The airport can further include transmitters 180 in various locations to provide the audio or visual component of the announcements to devices that tune into or connect to the broadcast system 150.

The secondary device 190 is a device other than the user device 102 and the broadcast system 150. The secondary device 190 can nonetheless also be a device of the user or recipient of the user device 102 (e.g., a device that the user owns, controls, or operates). For example, the secondary device 190 is a computing device associated with the recipient of the user device 102 such as a phone, tablet, or wearable device, among other forms.

In the illustrated example, the secondary device 190 includes, among other components, one or more processors 110, memory 116, one or more sensors 120, a receiver 130 and a user device application 152 (e.g., encoded in the memory 116 and executed by the one or more processors 110 of the secondary device 190) memory 116, and a user device application 192. The one or more processors 110, sensors 120, and memory 116 can be as described above in relation to the user device 102. The user device application 192 is a software application that operates on the secondary device 190 and cooperates with the user device 102 directly or via an intermediary device. In an example, the user device application 192 controls the user device 102 (e.g., based on input received from the recipient) and obtains data from the user device 102 and other devices. The secondary device 190 connects to the user device 102 using, for example, a wireless radiofrequency communication protocol (e.g., BLUETOOTH). The secondary device 190 transmits data to or receives data from the user device 102 over such a connection. In examples where the user device 102 is an auditory device, the secondary device 190 can stream audio to user device 102 for stimulating the recipient of the user device 102 using the stimulator 140. In some examples, the user device application 192 provides a user interface over with the user can modify settings of the user device 102 as well as one or more parameters of techniques described herein.

Figure 2:
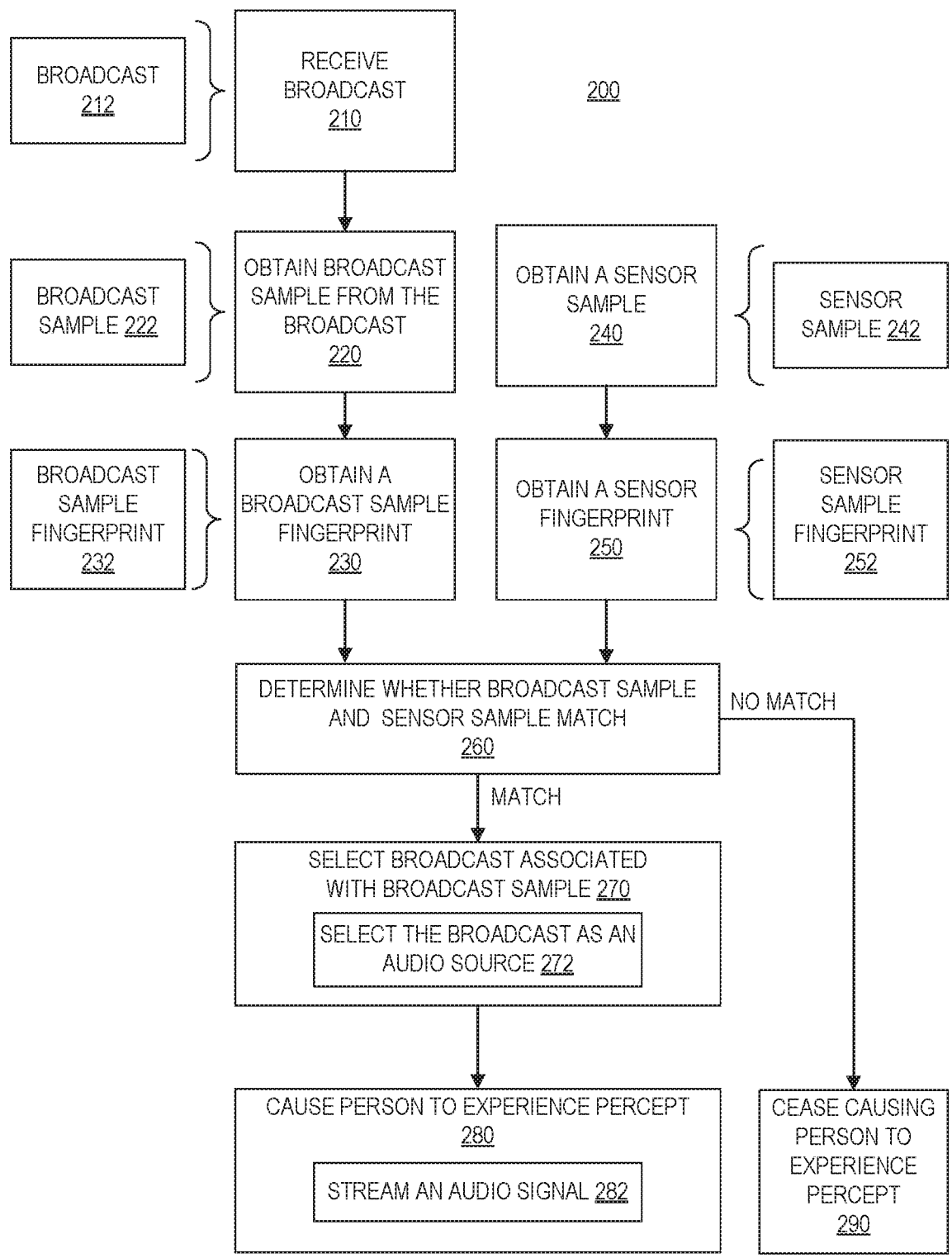
FIG. 2 illustrates an example method.

One or more of the components of the system 100 can cooperate or coordinate to perform one or more operations described herein, such as the example method of FIG. 2.

Example Method

FIG. 2 illustrates an example method 200. The operations of the method 200 can be performed by one or more of the components of the system 100. In some examples, the method 200 is performed when stimulation provided by the user device 102 is not being based on a broadcast. In some examples, the method 200 is performed when the stimulation provided by the user device 102 is being based on a broadcast, such as to ensure that the broadcast is still relevant.

Operation 210 includes receiving a broadcast 212. For example, the broadcast 212 is received by the receiver 130 of the user device 102 or the secondary device 190. In an example, the broadcast 212 is received as a wireless signal, such as radio waves having a frequency between 2.4 GHz and 2.5 GHz that encode a signal.

In an example, the broadcast 212 is generated by the transmitter 180 of the broadcast system 150. The broadcast 212 is able to be sent using any of a variety of protocols, such as WI-FI (e.g., broadcast as radio waves of between 2.40 GHz and 2.50 GHz or between 5.00 GHz and 6 GHz that encode a signal in compliance with IEEE 802.11), BLUETOOTH (e.g., broadcast as radio waves of between 2.4 GHz and 2.5 GHz that encode a signal in compliance with the BLUETOOTH 5.2 specification), FM (e.g., broadcast as radio waves of between 76.0 MHz and 108.0 MHz that encode a signal by modulating frequency), other techniques, or combinations thereof.

In some examples, receiving the broadcast 212 includes performing one or more preparatory steps. In an example, prior to receiving the broadcast 212, one or more components of the user device 102 tune to a frequency of the broadcast 212. In an example, a portion of the broadcast 212 is received, and then one or more components of the user device 102 preform one or more operations to connect to the broadcast 212 fully, such as operations that permit the user device 102 to usefully receive the intended content of the broadcast 212 (e.g., the audio or visual content). For instance, the broadcast 212 provides an identifier of a broadcast 212 (e.g., a WI-FI service set identifier) and the user device 102 takes one or more actions to connect to or pair with the broadcast 212 or the source of the broadcast 212. In some instances, the user device 102 authenticates with the source of the broadcast 212 such as by providing an identifier or passcode.

Operation 220 includes obtaining a broadcast sample 222 from the broadcast 212. In an example, the obtaining includes storing a portion of broadcast content provided over the broadcast 212. For example, the broadcast sample 222 is a portion of audio or video data provided over the broadcast 212. The broadcast sample 222 can be any of a variety of lengths.

In many examples, the broadcast 212 transmits a streaming media signal conveying media content configured to be consumed (e.g., played) substantially contemporaneously (e.g., in real time) with receiving the streaming media signal, rather than, for example, transmitting a media content file for playback at a later time (e.g., providing the media content file for the receiving device to download). Nonetheless, while in some examples the broadcast sample 222 is a short snippet of the streaming media signal, in other examples, the broadcast sample 222 can be obtained as a relatively longer, buffered or downloaded signal.

Operation 230 includes obtaining a broadcast sample fingerprint 232 from the broadcast sample 222. The broadcast sample fingerprint 232 is a portion of the broadcast sample 222 or a representation of the broadcast sample 222 configured for comparison with another fingerprint (e.g., a sensor sample fingerprint). The broadcast sample fingerprint 232 can be formed in any of a variety of ways.

In an example, obtaining the broadcast sample fingerprint 232 includes characteristic landmarks or features within the sample. Such landmarks can be, for example, particularly high or low volume, frequency, or energy sections within the broadcast sample 222. The broadcast sample fingerprint 232 can further be applied to patterns within the broadcast sample 222. For instance, the fingerprint 232 can indicate that certain landmarks occur a particular time apart and have certain characteristics. In a specific example, the fingerprint 232 is data indicating that the broadcast sample 222 includes a 0.05 second segment having a volume 50% greater than a mean volume of the sample 222, then a 0.1 second segment having a volume 50% less than the mean volume, and then a 0.25 second segment having a volume 25% greater than the mean volume of the sample. In an example, the broadcast sample fingerprint 232 is a spectrogram or is derived from a spectrogram.

In an example, obtaining the broadcast sample fingerprint 232 includes performing speech-to-text processing on the broadcast sample. In addition or instead, obtaining the broadcast sample fingerprint 232 includes performing content recognition on the broadcast sample. For instance, the broadcast sample 222 is provided as input to an artificial intelligence system configured to recognize sounds (e.g., identifying sounds as being of a particular type or category, such as birdsong, human speech, music, etc.) or visuals (e.g., visuals of a particular type or category, such as birds, people, or musical instruments) conveyed by the broadcast sample 222. The recognized output can be used as the broadcast sample fingerprint 232.

Other techniques can be used to generate the fingerprint 232, such as various techniques for generating fingerprints that are known in the art. In an example, a perceptual hashing algorithm is used. Further, some organizations offer open source libraries for comparing content or generating perceptual hashes. Examples include PHASH by AETILIUS, INC.

Operation 240 includes obtaining a sensor sample 242. In an example, the obtaining includes storing a portion of sensor data provided by a sensor 120. Where the sensor 120 is a camera, obtaining the sensor sample 242 includes obtaining the sensor sample 242 with or from a camera. Where the sensor 120 is a microphone, obtaining the sensor sample 242 includes obtaining the sensor sample 242 with or from a microphone. Depending on the implementation, different devices obtain the sensor sample 242, such as the user device 102 implemented as a visual prosthesis, consumer device, or auditory prosthesis. In another implementation, the secondary device 190 obtains the sensor sample 242, such as the secondary device 190 implemented as a phone, tablet, laptop, or wearable computing device. While in some examples the sensor sample 242 is a short snippet of the streaming media signal, in other examples, the sensor sample 242 can be obtained as a relatively longer, buffered or downloaded signal.

In some examples, operation 240 includes one or more aspects described below in conjunction with operation 340 of FIG. 3.

Operation 250 includes obtaining a sensor sample fingerprint 252 from the sensor sample 242. In many examples, the sensor sample fingerprint 252 is obtained using the same or substantially similar technique to the one or more techniques used to generate the broadcast sample fingerprint 232 as described above in conjunction with operation 230.

Operation 260 includes determining whether the broadcast sample 222 and the sensor sample 242 match. In an example, the operation 260 determines that the broadcast sample 222 and the sensor sample 242 match responsive to determining that the broadcast sample fingerprint 232 and the sensor sample fingerprint 252 have a level of similarity within a threshold amount. In some examples, the threshold is configurable by the user (e.g., via a setting screen in the user device application 192). In some examples, the threshold is configured to overcome a level of environmental noise around the user. For instance, the sensor sample 242 is more likely to pick up ambient noise that would not be present in the broadcast sample 222. Thus, the comparison can be configured to account for such a difference. In some examples, the threshold is automatically adjusted based on an amount of ambient noised detected by the sensor 130 or based on a currently-selected scene by a scene classifier of the user device 102.

In some examples, determining whether the broadcast sample 222 is a desired broadcast 212 includes asking the user. For example, the user device 102 can notify the user that a potentially acceptable broadcast 212 has been found. The user device 102 can then ask the user whether the user would like to try that broadcast 212. Then, the use device 102 can stimulate the user based on data received over the broadcast 212 for a period of time and then ask the user if her or she would like to continue to use the broadcast as a stimulation source. If the user agrees, then it can be determined that the broadcast sample 222 is a desired broadcast 212. In such an example, the sensor sample 242 and fingerprint 252 can be discarded, not collected, or unused. In further examples, the sensor sample 242 and fingerprint 252 are used as an initial, rough comparison and then, responsive to the initial comparison passing, the user is asked.

In some examples, the determining of a match is performed in substantially real-time on the broadcast sample 222 and the sensor sample 242 as they are received. In some examples, processing is performed to account for delay between the two samples 222, 242. In other examples, the determining of a match is performed at a slight delay, such as to permit processing on relatively longer samples 222, 242.

In some examples, responsive to operation 260 indicating that there is a match, the flow of the method 200 moves to operation 270. In some examples, responsive to operation 260 indicating that there is not a match, the flow of the method moves to operation 290. In some examples, responsive to operation 260 indicating that there is not a match, the method 200 ends or loops back to the beginning. Returning to the beginning can occur after a delay, a detected change in environment (e.g., a change in location as determined based on a location sensor or a change in a currently-classified scene), or in response to manual prompting by the user. In some instances, the broadcast 212 is one of multiple different potential broadcasts 212. In such an example, responsive to operation 260 indicating that there is not a match, the method 200 returns to the beginning to try a different broadcast, such as using one or more techniques described in more detail in the method 300 of FIG. 3, below.

Operation 270 includes selecting a broadcast 212 associated with the broadcast sample 222. In an example, the operation 270 is performed responsive to the broadcast sample 222 and the sensor sample 242 matching in operation 260. For example, the selecting includes selecting the broadcast 212 as the source of data on which stimulation provided by the stimulator 140 is based. In some examples, operation 270 includes operation 272. Operation 272 includes selecting the broadcast 212 as an audio source, such as an audio source used to cause a person to experience an audio percept. In addition or instead, operation 270 includes selecting the broadcast 212 as a visual source used to cause the recipient of the user device to experience a visual percept.

In some examples, operation 270 includes changing a mode of operation of the user device 102. For example, the user device 102 first operates in a sensor mode where the user device 102 provides stimulation based on output from a sensor and then, as part of selecting the broadcast, the user device 102 switches to operating in a broadcast mode where the user device 102 provides stimulation based on the broadcast 212. A non-limiting example of operating a device in a microphone mode and an accessory mode is described in U.S. Pat. No. 8,706,245, which was previously incorporated herein by reference. In an example, techniques described in U.S. Pat. No. 8,706,245 relating to the accessory mode can be applied to operating based on the selected broadcast 212 and techniques relating to the microphone mode can be applied to operating based on the sensor 130.

In an example, the determining (operation 260) and the selecting (operation 270) are performed by a secondary device 190, such as automatically or manually by the secondary device 190. The operations 260, 270 can be performed by any of a variety of devices or components of systems. In an example, the operation 260, 270 are performed by an implanted or external component of an auditory prosthesis (e.g., the user device 102 implemented as an auditory prosthesis).

Operation 280 includes causing a person to experience a percept. In an example, the percept is an audio percept, a visual percept, or both audio and visual percepts based on an audio signal or visual signal of the broadcast 212. In an example, the operation 280 includes generating stimulation using the stimulator 140. In an example, the operation 280 includes generating air-conducted vibrations, bone-conducted vibrations, or electrical stimulation configured to cause the recipient to experience an auditory percept. In an example, operation 280 includes generating visual signals or electrical stimulation configured to cause the recipient to experience a visual percept.

Operation 282 includes to stream an audio signal. For example, a secondary device 190 streams the audio signal to a separate hearing device (e.g., the user device 102 configured as a hearing device), such as an audio signal that causes the separate hearing device to stimulate the person to experience the audio percept. In some examples, the secondary device 190 does not stream the audio signal for a long duration. In some examples, the secondary device 190 initially selects the broadcast 212 and then transfers the broadcast (e.g., via a sync signal) to the user device 102 such that the user device 102 directly receives the broadcast 212 from the broadcast system 150 rather than through the secondary device 190 as an intermediary. In other examples, causing the person to experience the percept includes the secondary device 190 acting as an intermediary to provide an audio signal based on the broadcast 212 to the user device 102 to cause the user device 102 to stimulate the user based thereon.

In some examples, the user device 102 has different processing pathways or settings for signals obtained from the sensors 120 and the receiver 130. A non-limiting example of such an arrangement is described in U.S. Pat. No. 8,706,245, which was previously incorporated herein by reference.

Operation 290 includes to cease causing a person to experience a percept based on the broadcast 212. For instance, the user device 102 already causes a user to experience a percept based on the broadcast 212. But, in some examples (e.g., the person walks away from an area where the broadcast 212 is relevant but nonetheless the broadcast is being received), it can be desirable to cease causing a person to experience a percept. As illustrated, the operation 290 is performed responsive to the broadcast sample 222 and the sensor sample 242 not matching in operation 260. In some examples, further criteria exist, such as the broadcast sample 222 and the sensor sample 242 not matching more than a threshold number of times or not matching for longer than a threshold amount of time.

In some examples, responsive to the broadcast sample 222 and the sensor sample 242 not matching, the user device 102 or the secondary device 190 asks the user whether the user would like to continue to use the selected broadcast 212. Then, responsive to the user indicating that he or she does not want to continue to use the selected broadcast 212, operation 290 is performed.

In some examples, further responsive to the broadcast sample 222 and the sensor sample 242 not matching, broadcast 212 is excluded from consideration from future analyses as a non-matching broadcast (e.g., to avoid repeatedly trying to see if the broadcast 212 matches). In some examples, the broadcast 212 is excluded from consideration after a certain number of failed attempts.

Computer Readable Medium

Figure 3:
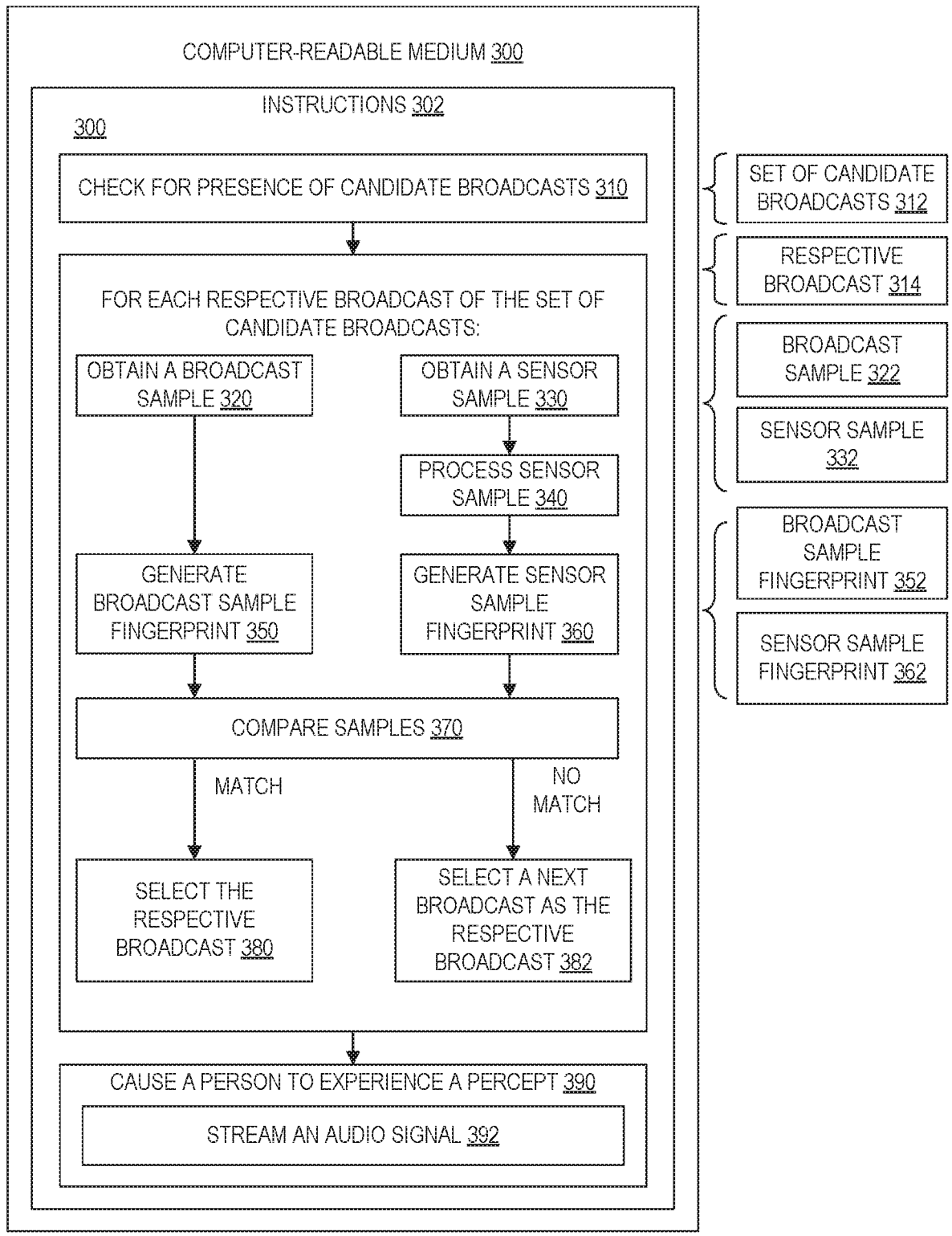
FIG. 3 illustrates a computer-readable medium having instructions stored thereon that, when executed by one or more processors, cause the one or more processors to perform a method that includes one or more operations.

FIG. 3 illustrates a computer-readable medium 300 having instructions 302 stored thereon that, when executed by one or more processors 110, cause the one or more processors 110 to perform a method 300 that includes one or more operations.

The computer-readable medium 300 is a component of a device of the system 100, such as the user device 102 or the secondary device 190. Depending on the implementation, the computer-readable medium 300 is a component of various devices, such as a visual prosthesis, auditory prosthesis, or a consumer audio device. The computer-readable medium is a transitory or non-transitory computer-readable medium. In an example, the computer-readable medium 300 is a component of an implanted or external component of an auditory prosthesis selected from the group consisting of: a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, a tooth-anchored hearing device, and a personal sound amplification product.

The instructions 302 are processor-executable program instructions that, when executed by the one or more processors 110 cause the one or more processors 110 to perform actions or operations, such as the described in relation to the methods herein. The instructions 302 can configure the one or more processors 110 to perform operations.

Operation 310 includes to check for a set of candidate broadcasts 312. In an example, the operation 310 is performed automatically, such as at a predetermined time interval. In some examples, the check is not merely whether the candidate broadcasts 312 exist, but whether each respective broadcast 314 meet threshold criteria. For instance, the threshold criteria can include the ability of the device performing the operations to usefully obtain data from the respective broadcast 314 (e.g., the respective broadcast 314 is not passcode protected with an unknown password, encrypted, or in an incompatible format). The threshold criteria can further include the broadcast 314 including useful data. For instance, the user device 102 may be configured to cause the recipient to experience auditory precepts, and the threshold criteria can be that the respective broadcast 314 conveys auditory data.

Then, for each respective broadcast 314 in the set of candidate broadcasts 312, one or more of operations 320, 330, 340, 350, 360, 370, and 380 are performed.

Operation 320 includes to obtain a broadcast sample 322 from the respective broadcast 314. In an example, the operation 320 includes to obtain data from a component configured to receive the respective broadcast 314 as radio waves of between 2.4 GHz and 2.5 GHz that encode a signal. In an example, the operation 320 includes to obtain data from a receiver compatible with at least the BLUETOOTH 5.2 specification. In an example, the operation 320 includes to store a portion of respective broadcast content provided over the respective broadcast 314. Operation 320 can include one or more aspects of operation 220 as described above.

Operation 330 includes to obtain a sensor sample 332 from a sensor 120. In an example, the operation 330 includes to store a portion of sensor data provided by the sensor 120. Operation 330 can include one or more aspects of operation 240 as described above.

Operation 340 includes to process the sensor sample 332. In some examples, the user device 102 is a device configured to obtain auditory input and provide an output based thereon, such as a hearing aid, cochlear implant, other auditory prostheses, and certain consumer audio devices (e.g., having passthrough audio features to bypass noise isolation). Such devices 102 can perform processing on the audio such as noise cancelation, beamforming, equalization, or other processing. Additional techniques include: gain adjustments (e.g., multichannel gain control), noise reduction operations, or signal enhancement operations (e.g., speech enhancement, wind reduction), other operations, or combinations thereof, in one or more of the channels. Noise reduction can include processing operations that identify unwanted components of a signal (e.g., noise components), and then subsequently reduce the presence of these unwanted components. Signal enhancement can refer to processing operations that identify the target signals (e.g., speech or music) and then subsequently increase the presence of these target signal components. Speech enhancement is a particular type of signal enhancement. While such techniques can be beneficial, where sensor samples 332 are obtained from a same audio processing pathway, such processing techniques can undesirably affect the sensor sample 332 for the purposes of comparing the sensor sample 332 (or a fingerprint thereof) with data received over the broadcast 314. For instance, the sensor sample 332 is affected such that the sensor sample 332 is incorrectly classified as not matching the broadcast sample 322. In other instances, certain processing of output from the sensor 120 beneficially cleans up the sensor sample 332 to improve the ability of the sensor sample 332 to correctly match or not match the broadcast sample 322. For example, the equalization to correct for bias in the output of the sensor 120, wind noise cancelation, or other processing can be beneficial. In some examples, the sensor sample 332 is processed in a same way as other sensor samples of the user device 102 (e.g., during normal use where output from the sensors 130 is used to provide stimulation), is processed in partially the same way (e.g., certain processing is performed and certain processing that would normally be performed is not performed), is processed in a different way (certain processing not normally applied is applied), or is substantially unprocessed. In an example, operation 340 includes processing the sensor sample 332 by applying beamforming processing to the sensor sample 332 or applying wind noise reduction to the sensor sample 332. For instance, the sensor sample 332 begins as raw output from the sensor 120 and is processed by applying one or both of beamform processing and wind noise reduction.

In an example, to process the sensor sample 332 includes to apply a first sound processing technique to an audio signal obtained from the sensor 120 to form a first processed audio signal. For instance, the first sound processing technique can include wind noise cancelation or a processing technique that does not substantially negatively affect the ability to compare the sensor sample 332 and the broadcast sample 322. Then, a second sound processing technique is applied to the first processed audio signal to form a second processed audio signal. The second sound processing technique is a sound processing technique that is likely to negatively affect the ability to compare the sensor sample 332 and the broadcast sample 322. Then the user device 102 stimulates a recipient of the sensory prosthesis using the second processed audio signal, and the first processed audio signal is used as the sensor sample 332. For instance, to determine whether the broadcast sample 322 and the sensor sample 332 match includes to compare the broadcast sample 322 with the first processed audio signal.

Operation 350 includes to generate a broadcast sample fingerprint 352 from the broadcast sample 322. Operation 360 includes to generate a sensor sample fingerprint 362 from the sensor sample 332. These operations 350, 360 can include one or more aspects as described above in relation to operations 230 and 250, above.

Operation 370 includes to compare 370 the broadcast sample 322 and the sensor sample 332. In an example, comparing the broadcast sample 322 and the sensor sample 332 includes determining whether the samples 322, 332 match responsive to the broadcast sample fingerprint 352 and sensor sample fingerprint 362 having more than a threshold amount of similarity. The operation 370 can include one or more aspects as described above in relation to operation 260.

Responsive to the operation 370 indicating that the broadcast sample 322 and the sensor sample 332 match, the flow of the method 300 moves to operation 380. Responsive to the operation 370 indicating that the broadcast sample 322 and the sensor sample 332 not matching, the flow of the method 300 moves to operation 382.

Operation 380 includes to select the respective broadcast 314 responsive to the comparing (operation 370) indicating that the broadcast sample 322 and the sensor sample 332 match. For instance, the respective broadcast 314 as an audio source used to cause a person to experience an audio percept. The operation 380 can include one or more aspects as described above in relation to operation 270.

Operation 382 includes to select a next broadcast 212 of the set of candidate broadcasts 312 as the respective broadcast 314 and the operations 320, 330, 340, 350, 360 are performed for the new respective broadcast 314. If the respective broadcast was the last respective broadcast 314 of the set of candidate broadcasts 312 (e.g., there is no next broadcast), then the flow of the method 300 can return to operation 310.

After selecting the respective broadcast in operation 380, the flow of the method 300 moves to operation 390.

Operation 390 includes to cause a person to experience an audio percept based on the selected respective broadcast 314. In an example, the operation 390 includes operation 392. Operation 392 includes to stream an audio signal to a hearing device to cause the hearing device to stimulate the person to experience the audio percept. The operation 390 can include one or more aspects as described above in relation to operation 280.

Processors

Figure 4:
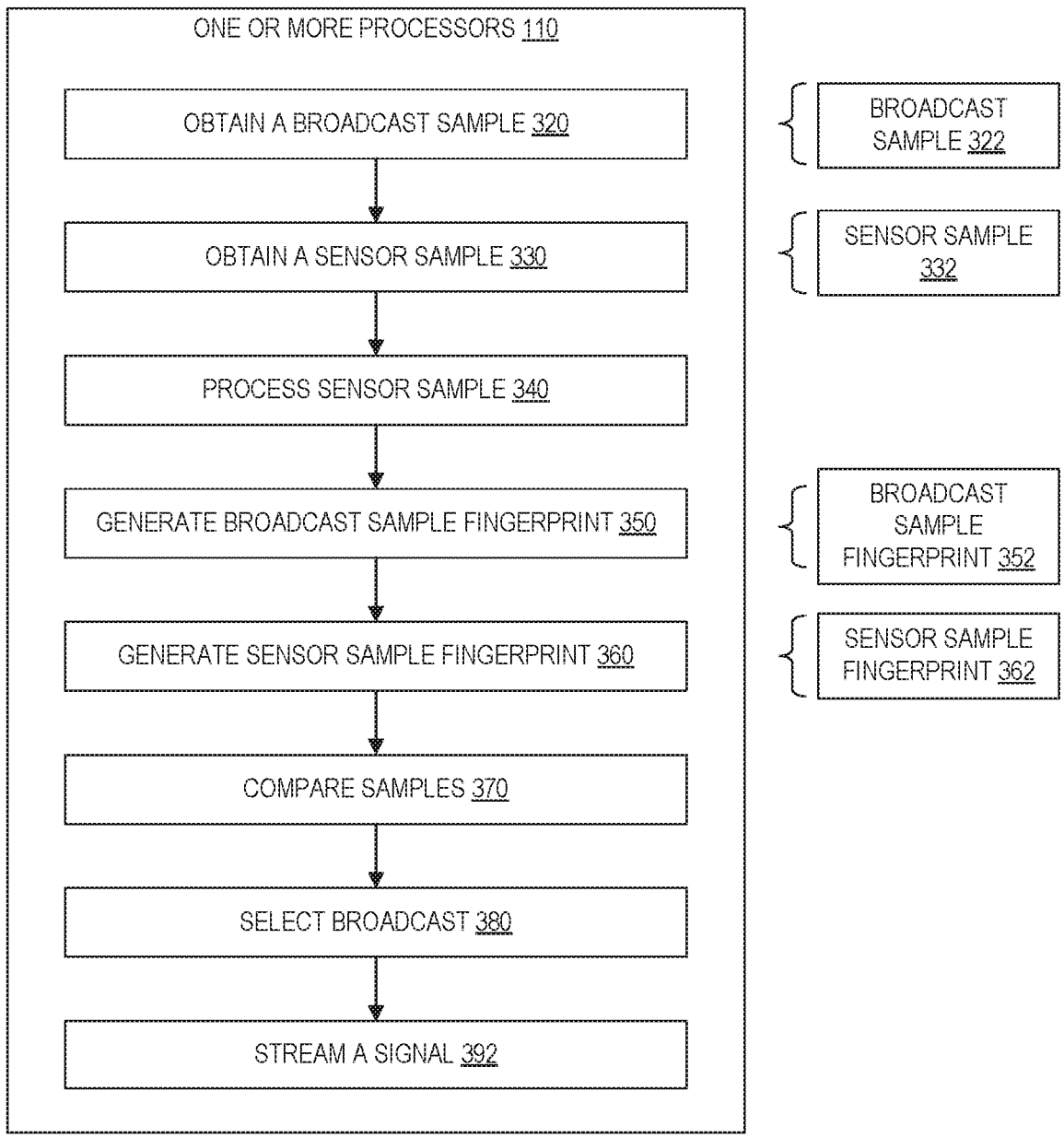
FIG. 4 illustrates one or more processors configured to perform one or more operations.

FIG. 4 illustrates one or more processors 110 configured to perform one or more operations. The one or more processors 110 can be communicatively coupled to memory having stored thereon instructions that so configure the one or more processors 110. For instance, the memory can include instructions thereon that, when executed by the one or more processors 110, cause the one or more processors 110 to perform the one or more operations herein. In an example, the operations include operations 320, 330, 340, 350, 360, 370, 380, and 392, such as described in FIG. 3. In some examples, the one or more processors 110 are configured to perform fewer or additional operations, such as other operations described herein.

Example Computing System

Figure 5:
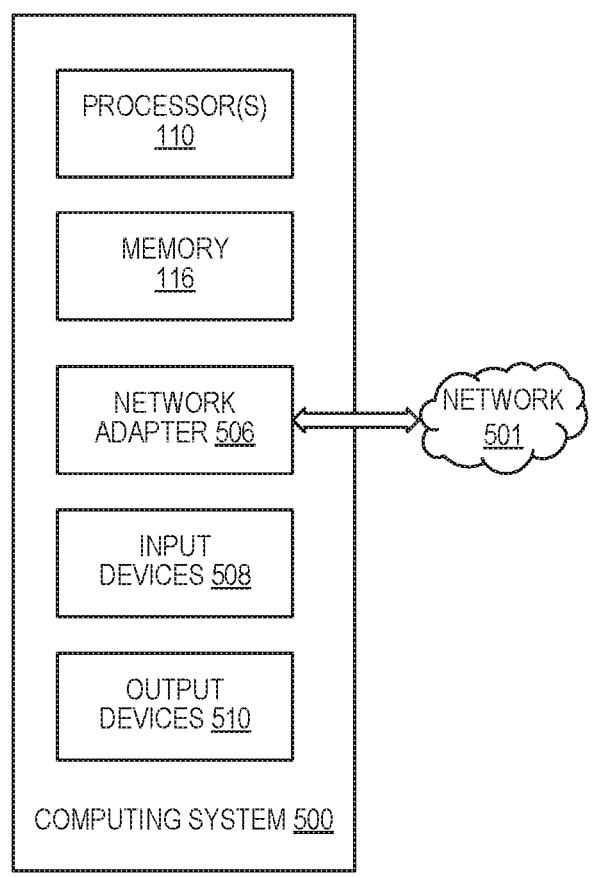
FIG. 5 illustrates an example of a suitable computing system with which one or more of the disclosed examples can be implemented.

FIG. 5 illustrates an example of a suitable computing system 500 with which one or more of the disclosed examples can be implemented. Computing systems, environments, or configurations that suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 500 can be a single virtual or physical device operating in a networked environment over communication links to one or more remote devices. In examples, the user device 102, the broadcast system 150, and the secondary device 190, include one or more components or variations of components of the computing system 500.

In its most basic configuration, computing system 500 includes one or more processors 110 and memory 116, which are described above in relation to FIG. 1. In the illustrated example, the system 500 further includes a network adapter 506, one or more input devices 508, and one or more output devices 510. The system 500 can include other components, such as a system bus, component interfaces, a graphics system, a power source (e.g., a battery), among other components.

The network adapter 506 is a component of the computing system 500 that provides network access. The network adapter 506 can provide wired or wireless network access and can support one or more of a variety of communication technologies and protocols, such as ETHERNET, cellular, BLUETOOTH, near-field communication, and RF (Radiofrequency), among others. The network adapter 506 can include one or more antennas and associated components configured for wireless communication according to one or more wireless communication technologies and protocols.

The one or more input devices 508 are devices over which the computing system 500 receives input from a user. The one or more input devices 508 can include physically-actuatable user-interface elements (e.g., buttons, switches, or dials), touch screens, keyboards, mice, pens, and voice input devices, among others input devices.

The one or more output devices 510 are devices by which the computing system 500 can provide output to a user. The output devices 510 can include, displays, speakers, and printers, among other output devices.

Example Devices

As previously described, the technology disclosed herein can be applied in any of a variety of circumstances and with a variety of different devices. For example, the user device 102 can take the form of a variety of different consumer devices or medical devices. Example consumer devices include headphones, earbuds, personal sound amplification products, wireless earbuds, or other consumer devices. Example medical devices include auditory prostheses and visual prostheses. Example auditory prostheses include one or more prostheses selected from the group consisting of: a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, and a tooth-anchored hearing device. Example visual prostheses include bionic eyes.

Specific example devices that can benefit from technology disclosed herein are described in more detail in FIGS. 6-8, below. For example, the techniques described herein can be used to select broadcasts for medical devices, such as an implantable stimulation system as described in FIG. 6, a cochlear implant as described in FIG. 7, or a retinal prosthesis as described in FIG. 8.

Example Device—Implantable Stimulator System

Figure 6:
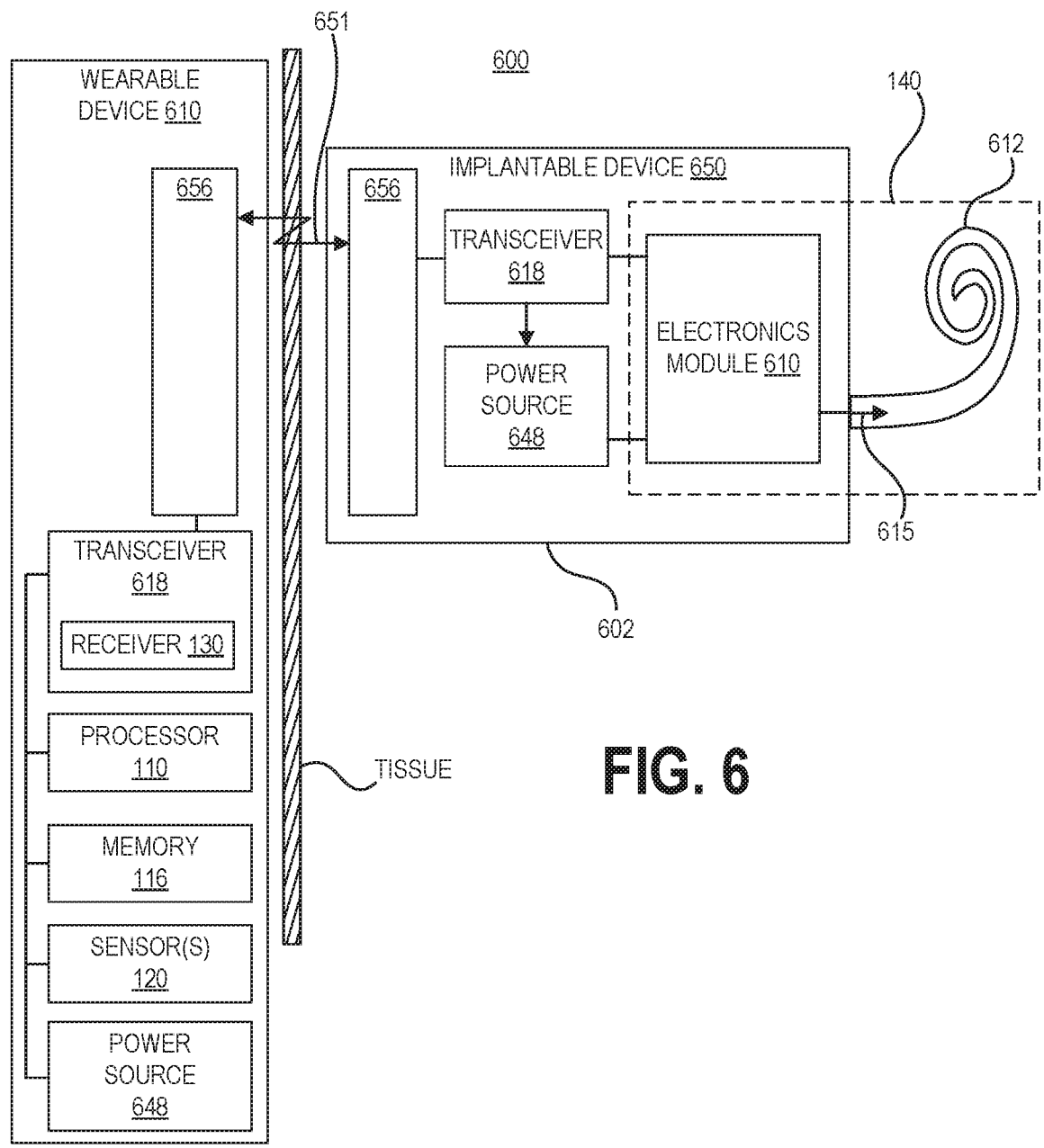
FIG. 6 is a functional block diagram of an implantable stimulator system that can benefit from the technologies described herein.

FIG. 6 is a functional block diagram of an implantable stimulator system 600 that can benefit from the technologies described herein. In an example, the user device 102 corresponds to the implantable stimulator system 600. The implantable stimulator system 600 includes a wearable device 610 acting as an external processor device and an implantable device 650 acting as an implanted stimulator device. In examples, the implantable device 650 is an implantable stimulator device configured to be implanted beneath a recipient's tissue (e.g., skin). In examples, the implantable device 650 includes a biocompatible implantable housing 602. Here, the wearable device 610 is configured to transcutaneously couple with the implantable device 650 via a wireless connection to provide additional functionality to the implantable device 650.

In the illustrated example, the wearable device 610 includes one or more sensors 120, a processor 110, memory 116, a transceiver 618, and a power source 648. The one or more sensors 120 can be units configured to produce data based on sensed activities. In an example where the stimulation system 600 is an auditory prosthesis system, the one or more sensors 120 include sound input sensors, such as a microphone. Where the stimulation system 600 is a visual prosthesis system, the one or more sensors 120 can include one or more cameras or other visual sensors. The processor 110 can be a component (e.g., a central processing unit) configured to control stimulation provided by the implantable device 650. The stimulation can be controlled based on data from the sensor 120, a stimulation schedule, or other data. Where the stimulation system 600 is an auditory prosthesis, the processor 110 can be configured to convert sound signals received from the sensor(s) 130 (e.g., acting as a sound input unit) into signals 651. The transceiver 618 is configured to send the signals 651 in the form of power signals, data signals, combinations thereof (e.g., by interleaving the signals), or other signals. The transceiver 618 can also be configured to receive power or data. Stimulation signals can be generated by the processor 110 and transmitted, using the transceiver 618, to the implantable device 650 for use in providing stimulation. In the illustrated example, the transceiver 618 includes the receiver 130.

In the illustrated example, the implantable device 650 includes a transceiver 618, a power source 648, a coil 656, and a stimulator 120 that includes an electronics module 610 and a stimulator assembly 124. The implantable device 650 further includes a hermetically sealed, biocompatible housing enclosing one or more of the components.

The electronics module 610 can include one or more other components to provide sensory prosthesis functionality. In many examples, the electronics module 610 includes one or more components for receiving a signal (e.g., from one or more of the sensors 120) and converting the signal into the stimulation signal 615. The electronics module 610 can further be or include a stimulator unit (e.g., stimulator unit 122). The electronics module 610 can generate or control delivery of the stimulation signals 615 to the stimulator assembly 612. In examples, the electronics module 610 includes one or more processors (e.g., central processing units or microcontrollers) coupled to memory components (e.g., flash memory) storing instructions that when executed cause performance of an operation. In examples, the electronics module 610 generates and monitors parameters associated with generating and delivering the stimulus (e.g., output voltage, output current, or line impedance). In examples, the electronics module 610 generates a telemetry signal (e.g., a data signal) that includes telemetry data. The electronics module 610 can send the telemetry signal to the wearable device 610 or store the telemetry signal in memory for later use or retrieval.

The stimulator assembly 612 can be a component configured to provide stimulation to target tissue. In the illustrated example, the stimulator assembly 612 is an electrode assembly that includes an array of electrode contacts disposed on a lead. The lead can be disposed proximate tissue to be stimulated. Where the system 600 is a cochlear implant system, the stimulator assembly 612 is insertable into the recipient's cochlea. The stimulator assembly 612 can be configured to deliver stimulation signals 615 (e.g., electrical stimulation signals) generated by the electronics module 610 to the cochlea to cause the recipient to experience a hearing percept. In other examples, the stimulator assembly 612 is a vibratory actuator disposed inside or outside of a housing of the implantable device 650 and configured to generate vibrations. The vibratory actuator receives the stimulation signals 615 and, based thereon, generates a mechanical output force in the form of vibrations. The actuator can deliver the vibrations to the skull of the recipient in a manner that produces motion or vibration of the recipient's skull, thereby causing a hearing percept by activating the hair cells in the recipient's cochlea via cochlea fluid motion.

The transceivers 618 can be components configured to transcutaneously receive and/or transmit a signal 651 (e.g., a power signal and/or a data signal). The transceiver 618 can be a collection of one or more components that form part of a transcutaneous energy or data transfer system to transfer the signal 651 between the wearable device 610 and the implantable device 650. Various types of signal transfer, such as electromagnetic, capacitive, and inductive transfer, can be used to usably receive or transmit the signal 651. The transceiver 618 can include or be electrically connected to the coil 656.

The coils 656 can be components configured to receive or transmit a signal 651, typically via an inductive arrangement formed by multiple turns of wire. In examples, in addition to or instead of a coil, other arrangements are used, such as an antenna or capacitive plates. The magnets can be used to align respective coils 656 of the wearable device 610 and the implantable device 650. For example, the coil 656 of the implantable device 650 is disposed in relation to (e.g., in a coaxial relationship) with an implantable magnet set to facilitate orienting the coil 656 in relation to the coil 656 of the wearable device 610 via the force of a magnetic connection. The coil 656 of the wearable device 610 can be disposed in relation to (e.g., in a coaxial relationship) with a magnet set.

The power source 648 can be one or more components configured to provide operational power to other components. The power source 648 can be or include one or more rechargeable batteries. Power for the batteries can be received from a source and stored in the battery. The power can then be distributed to the other components of the implantable device 650 as needed for operation.

Example Device—Cochlear Implant

Figure 7:
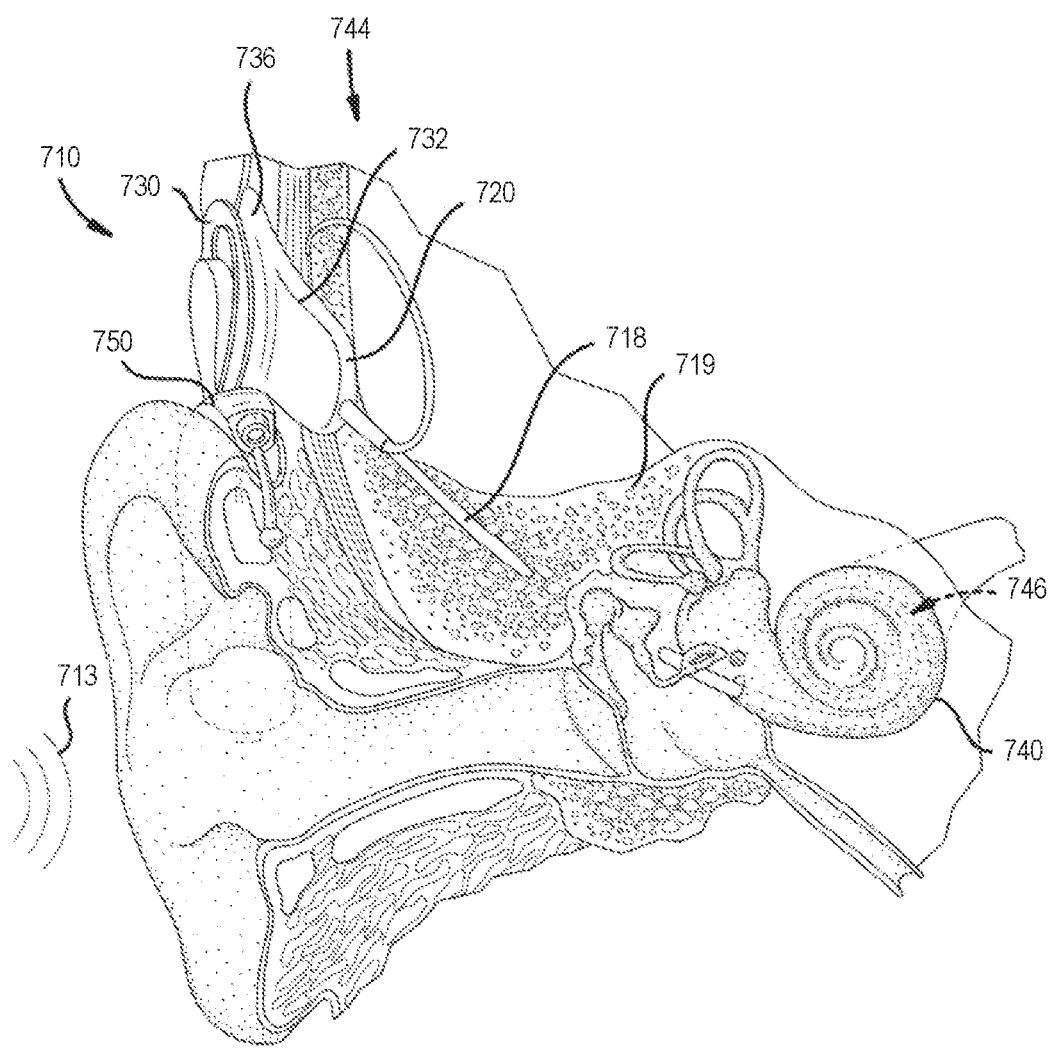
FIG. 7 illustrates an example cochlear implant system that can benefit from use of the technologies disclosed herein.

FIG. 7 illustrates an example cochlear implant system 710 that can benefit from use of the technologies disclosed herein. For example, the cochlear implant system 710 can be used to implement the user device 102. The cochlear implant system 710 includes an implantable component 744 typically having an internal receiver/transceiver unit 732, a stimulator unit 720, and an elongate lead 718. The internal receiver/transceiver unit 732 permits the cochlear implant system 710 to receive signals from and/or transmit signals to an external device 750. The external device 750 can be a button sound processor worn on the head that includes a receiver/transceiver coil 730 and sound processing components. Alternatively, the external device 750 can be just a transmitter/transceiver coil in communication with a behind-the-ear device that includes the sound processing components and microphone.

The implantable component 744 includes an internal coil 736, and preferably, an implanted magnet fixed relative to the internal coil 736. The magnet can be embedded in a pliable silicone or other biocompatible encapsulant, along with the internal coil 736. Signals sent generally correspond to external sound 713. The internal receiver/transceiver unit 732 and the stimulator unit 720 are hermetically sealed within a biocompatible housing, sometimes collectively referred to as a stimulator/receiver unit. Included magnets can facilitate the operational alignment of an external coil 730 and the internal coil 736 (e.g., via a magnetic connection), enabling the internal coil 736 to receive power and stimulation data from the external coil 730. The external coil 730 is contained within an external portion. The elongate lead 718 has a proximal end connected to the stimulator unit 720, and a distal end 746 implanted in a cochlea 740 of the recipient. The elongate lead 718 extends from stimulator unit 720 to the cochlea 740 through a mastoid bone 719 of the recipient. The elongate lead 718 is used to provide electrical stimulation to the cochlea 740 based on the stimulation data. The stimulation data can be created based on the external sound 713 using the sound processing components and based on sensory prosthesis settings.

In certain examples, the external coil 730 transmits electrical signals (e.g., power and stimulation data) to the internal coil 736 via a radio frequency (RF) link. The internal coil 736 is typically a wire antenna coil having multiple turns of electrically insulated single-strand or multi-strand platinum or gold wire. The electrical insulation of the internal coil 736 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Device—Retinal Prosthesis

Figure 8:
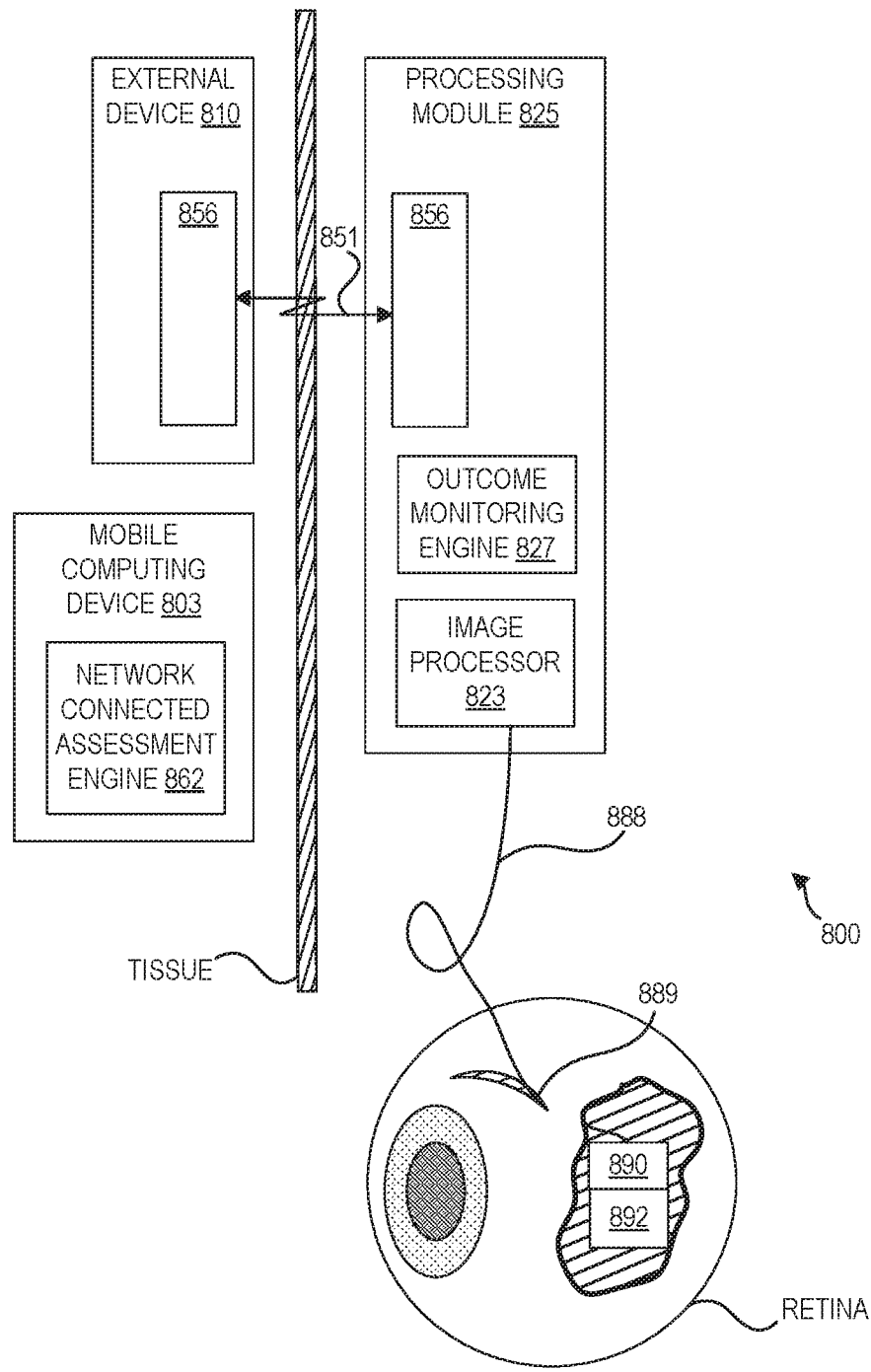
FIG. 8 illustrates a retinal prosthesis system that comprises an external device, a retinal prosthesis and a mobile computing device.

FIG. 8 illustrates a retinal prosthesis system 801 that comprises an external device 810, a retinal prosthesis 800 and a mobile computing device 803. The retinal prosthesis system 801 can correspond to the user device 102. The retinal prosthesis 800 comprises a processing module 825 and a retinal prosthesis sensor-stimulator 890 is positioned proximate the retina 891 of a recipient. The external device 810 and the processing module 825 can both include transmission coils 856 aligned via respective magnet sets. Signals 851 can be transmitted using the coils 856.

In an example, sensory inputs (e.g., photons entering the eye) are absorbed by a microelectronic array of the sensor-stimulator 890 that is hybridized to a glass piece 892 including, for example, an embedded array of microwires. The glass can have a curved surface that conforms to the inner radius of the retina. The sensor-stimulator 890 can include a microelectronic imaging device that can be made of thin silicon containing integrated circuitry that convert the incident photons to an electronic charge.

The processing module 825 includes an image processor 823 that is in signal communication with the sensor-stimulator 890 via, for example, a lead 888 which extends through surgical incision 889 formed in the eye wall. In other examples, processing module 825 is in wireless communication with the sensor-stimulator 890. The image processor 823 processes the input into the sensor-stimulator 890, and provides control signals back to the sensor-stimulator 890 so the device can provide an output to the optic nerve. That said, in an alternate example, the processing is executed by a component proximate to, or integrated with, the sensor-stimulator 890. The electric charge resulting from the conversion of the incident photons is converted to a proportional amount of electronic current which is input to a nearby retinal cell layer. The cells fire and a signal is sent to the optic nerve, thus inducing a sight perception.

The processing module 825 can be implanted in the recipient and function by communicating with the external device 810, such as a behind-the-ear unit, a pair of eyeglasses, etc. The external device 810 can include an external light/image capture device (e.g., located in/on a behind-the-ear device or a pair of glasses, etc.), while, as noted above, in some examples, the sensor-stimulator 890 captures light/images, which sensor-stimulator is implanted in the recipient.

Similar to the above examples, the retinal prosthesis system 801 may be used in spatial regions that have at least one controllable network connected device associated therewith (e.g., located therein). As such, the processing module 825 includes a performance monitoring engine 827 that is configured to obtain data relating to a "sensory outcome" or "sensory performance" of the recipient of the retinal prosthesis 800 in the spatial region. As used herein, a "sensory outcome" or "sensory performance" of the recipient of a sensory prosthesis, such as retinal prosthesis 800, is an estimate or measure of how effectively stimulation signals delivered to the recipient represent sensor input captured from the ambient environment.

Data representing the performance of the retinal prosthesis 800 in the spatial region is provided to the mobile computing device 803 and analyzed by a network connected device assessment engine 862 in view of the operational capabilities of the at least one controllable network connected device associated with the spatial region. For example, the network connected device assessment engine 862 may determine one or more effects of the controllable network connected device on the sensory outcome of the recipient within the spatial region. The network connected device assessment engine 862 is configured to determine one or more operational changes to the at least one controllable network connected device that are estimated to improve the sensory outcome of the recipient within the spatial region and, accordingly, initiate the one or more operational changes to the at least one controllable network connected device.

* * *

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A method comprising:
   obtaining, at a user device, a broadcast sample of radio wave signals transmitted by a device in an environment of the user device;
   obtaining, at the user device, a sensor sample of streaming media signals transmitted by the device;
   determining, by the user device, that the broadcast sample and the sensor sample match; and
   selecting a broadcast associated with the broadcast sample responsive to the broadcast sample and the sensor sample match.

2. The method of claim 1, further comprising:
   obtaining a broadcast sample fingerprint from the broadcast sample; and
   obtaining a sensor sample fingerprint from the sensor sample,
   wherein determining that the broadcast sample and the sensor sample match include:
   determining that the broadcast sample and the sensor sample match responsive to determining that the broadcast sample fingerprint and the sensor sample fingerprint have a level of similarity within a threshold amount.

3. The method of claim 1, wherein selecting the broadcast includes:
   selecting the broadcast as an audio source used to cause a person to experience an audio percept.

4. The method of claim 1, further comprising:
   causing a person to experience an audio percept based on an audio signal received over the broadcast.

5. The method of claim 4,
   wherein the determining and the selecting are performed by a computing device; and
   wherein causing the person to experience the audio percept includes:
   streaming, from the computing device to a separate hearing device, an audio signal that causes the separate hearing device to stimulate the person to experience the audio percept.

6. The method of claim 1, further comprising:
   receiving the broadcast as radio waves having a frequency between 2.4 GHz and 2.5 GHz that encode a signal.

7. The method of claim 1, further comprising:
   receiving the broadcast as radio waves of between 2.4 GHz and 2.5 GHz that encode a signal in compliance with the BLUETOOTH 5.2 specification.

8. The method of claim 1, wherein the determining and the selecting occur automatically.

9. The method of claim 1, further comprising:
   ceasing causing a person to experience percepts based on the broadcast responsive to the broadcast sample and the sensor sample failing to match.

10. The method of claim 1, wherein obtaining the broadcast sample further comprises obtaining the broadcast sample by storing a portion of broadcast content provided over the broadcast, and
    wherein obtaining the sensor sample further comprises obtaining the sensor sample by storing a portion of sensor data provided by a sensor.

11. A non-transitory computer-readable medium having instructions stored thereon that, when executed by one or more processors of a device, cause the one or more processors to:
    check for a set of candidate broadcasts transmitted over wireless radio signals by one or more broadcast devices in an environment of the device; and
    for each respective broadcast of the set of candidate broadcasts:
       obtain a broadcast sample from the respective broadcast;
       obtain a sensor sample from a sensor, wherein the sensor sample is a portion of a streaming media signal transmitted by a broadcast device of the one or more broadcast devices in the environment of the device;
       compare the broadcast sample and the sensor sample; and
       select the respective broadcast responsive to the comparing indicating that the broadcast sample and the sensor sample match.

12. The non-transitory computer-readable medium of claim 11, wherein the instructions, when executed by the one or more processors cause the one or more processors to, prior to comparing the broadcast sample and the sensor sample:
    process the sensor sample by: applying beamforming processing to the sensor sample or applying wind noise reduction to the sensor sample.

13. The non-transitory computer-readable medium of claim 11, wherein the instructions, when executed by the one or more processors cause the one or more processors to:
    automatically perform the check for the set of candidate broadcasts at a predetermined interval.

14. The non-transitory computer-readable medium of claim 11, wherein the instructions, when executed by the one or more processors cause the one or more processors to:
    generate a broadcast sample fingerprint from the broadcast sample; and
    generate a sensor sample fingerprint from the sensor sample; and
    wherein to compare the broadcast sample and the sensor sample includes to:
    determine that the broadcast sample and the sensor sample match responsive to
    determining that the broadcast sample fingerprint and the sensor sample fingerprint have a threshold amount of similarity.

15. The non-transitory computer-readable medium of claim 11, wherein to select the respective broadcast includes to:
    select the respective broadcast as an audio source used to cause a person to experience an audio percept.

16. The non-transitory computer-readable medium of claim 15, wherein the instructions, when executed by the one or more processors, cause the one or more processors to:

cause the person to experience an audio percept based on the respective broadcast,
wherein to cause the person to experience the audio percept includes to:
stream an audio signal to a hearing device to cause the hearing device to stimulate the person to experience the audio percept.

17. The non-transitory computer-readable medium of claim 11, wherein to obtain the broadcast sample from the respective broadcast includes to:
obtain data from a component configured to receive the respective broadcast as radio waves of between 2.4 GHz and 2.5 GHz that encode a signal.

18. The non-transitory computer-readable medium of claim 11, wherein to obtain the broadcast sample from the respective broadcast includes to:
obtain data from a receiver compatible with at least the BLUETOOTH 5.2 specification.

19. The non-transitory computer-readable medium of claim 11, wherein to obtain the broadcast sample includes to store a portion of broadcast content provided over the respective broadcast; and
wherein to obtain the sensor sample includes to store a portion of sensor data provided by the sensor.

20. The non-transitory computer-readable medium of claim 11, wherein the instructions, when executed by the one or more processors, further cause the one or more processors to cause a person to experience an audio percept based on an audio signal received over the respective broadcast.

21. A system comprising:
a sensory prosthesis;
a sensor configured to obtain streaming media signals from devices in an environment of the system;
a receiver configured to obtain radio wave signals from the devices in the environment of the system; and
one or more processors configured to:
obtain a broadcast sample from the receiver, wherein the broadcast sample is a radio wave signal;
obtain a sensor sample from the sensor, wherein the sensor sample is a streaming media signal;
determine whether the broadcast sample and the sensor sample match; and
select, as a source used by the sensory prosthesis to cause a person to experience a sensory percept, a broadcast associated with the broadcast sample responsive to the broadcast sample and the sensor sample matching.

22. The system of claim 21,
wherein the sensor is a microphone; and
wherein the sensory prosthesis is an auditory prosthesis.

23. The system of claim 21,
wherein the sensor is a camera; and
wherein the sensory prosthesis is a visual prosthesis.

24. The system of claim 21, wherein the sensory prosthesis comprises the sensor, the receiver; and the one or more processors.

25. The system of claim 21, further comprising:
a computing device,
wherein the computing device comprises the one or more processors.

26. The system of claim 25,
wherein the computing device further comprises the receiver; and
wherein the one or more processors are further configured to:
stream, from the computing device to the sensory prosthesis, a signal based on data from the broadcast.

27. The system of claim 21,
wherein the receiver is configured to receive the broadcast as radio waves of between 2.4 GHz and 2.5 GHz that encode a signal.

28. The system of claim 21, wherein the one or more processors are further configured to:
obtain a broadcast sample fingerprint from the broadcast sample;
obtain a sensor audio fingerprint from the sensor sample; and
determine that the broadcast sample and the sensor sample match responsive to determining that the broadcast sample fingerprint and the sensor audio fingerprint have a level of similarity within a threshold amount.

29. The system of claim 21,
wherein the sensory prosthesis is configured to:
process the sensor sample, wherein to process the sensor sample includes to:
apply a first sound processing technique to an audio signal obtained from the sensor to form a first processed audio signal;
apply a second sound processing technique to the first processed audio signal to form a second processed audio signal; and
stimulate a recipient of the sensory prosthesis using the second processed audio signal; and
wherein to determine whether the broadcast sample and the sensor sample match includes to compare the broadcast sample with the first processed audio signal.

30. The system of claim 21,
wherein the one or more processors are configured to obtain the broadcast sample by storing a portion of broadcast content provided over the broadcast.

* * * * *